(12) United States Patent
Jackson (10) Patent No.: US 6,224,596 B1
(45) Date of Patent: May 1, 2001

(54) SET SCREW FOR USE WITH OSTEOSYNTHESIS APPARATUS

(76) Inventor: Roger P. Jackson, 4706 West 86th St., Prairie Village, KS (US) 66207

( * ) Notice: Subject to any disclaimer, the term of this patent is extended or adjusted under 35 U.S.C. 154(b) by 0 days.

(21) Appl. No.: 09/095,687

(22) Filed: Jun. 10, 1998

Related U.S. Application Data (63) Continuation-in-part of application No. 08/778,765, filed on Jan. 6, 1997.

(51) Int. Cl.⁷ .................................................. A61B 17/56
(52) U.S. Cl. .................................................. 606/61; 411/5
(58) Field of Search ................................. 606/61, 72, 73; 411/3, 4, 5, 393

(56) References Cited

U.S. PATENT DOCUMENTS

| D. 200,217 | 2/1965 | Curtiss . |
|---|---|---|
| 791,548 | 6/1905 | Fischer . |
| 2,201,087 | 5/1940 | Hallowell . |
| 2,239,352 | 4/1941 | Cherry . |
| 2,295,314 | 9/1942 | Whitney . |
| 2,532,815 | 12/1950 | Kindsvatter . |
| 2,553,337 | 5/1951 | Shafer . |
| 2,778,265 | 1/1957 | Brown . |
| 2,877,681 | 3/1959 | Brown . |
| 2,927,332 | 3/1960 | Moore . |
| 3,143,029 | 8/1964 | Brown . |
| 3,370,341 | 2/1968 | Allsop . |
| 3,498,174 | 3/1970 | Schuster et al. . |
| 3,584,667 | 6/1971 | Reiland . |

(List continued on next page.)

FOREIGN PATENT DOCUMENTS

| 3630863 | 3/1988 | (DE) . |
|---|---|---|
| 373809 | 5/1989 | (DE) . |
| 195455 | 9/1986 | (EP) . |
| 172130 | 2/1987 | (EP) . |
| 276153 | 7/1988 | (EP) . |
| 465158 | 1/1992 | (EP) . |
| 2467312 | 4/1981 | (FR) . |
| 203508 | 9/1923 | (GB) . |
| PCT92/03100 | 3/1992 | (WO) . |
| PCT94/10927 | 5/1994 | (WO) . |
| PCT94/10944 | 5/1994 | (WO) . |
| PCT96/06576 | 3/1996 | (WO) . |

OTHER PUBLICATIONS

Two Drawings of Sofamor dated Mar. 10, 1994 and Sep. 20, 1994.

Photocopy of Sofamor Danek GDLH (TM) Posterior Spinal System Locking Screw and label, on sale at least one year prior to the filing of the present application.

*Primary Examiner*—David J. Isabella
(74) *Attorney, Agent, or Firm*—John C. McMahon (57) ABSTRACT

An improved set screw, for use in an osteosynthesis apparatus to secure and fix a spinal rod in the bore of the head of a bone screw, hook, connector or the like from translational or rotational motion, which comprises a head of hexagonal external cross-section and a lower portion having a threaded outer surface. The lower threaded portion includes a feature which facilitates subsequent removal of the lower threaded portion from the threaded bore in which it is secured. In a first embodiment, the feature facilitating removal, comprises a bore which extends completely through the screw, from top to bottom. The bore may be cylindrical and adapted to receive an easy out tool for removal of the lower threaded portion, or of a geometry which corresponds to the shape of an allen type wrench which may be inserted in the section of the bore extending into the lower threaded portion of the screw for use in removal of the lower threaded portion. In another embodiment, a flange is formed on the lower threaded portion of the screw at an upper end thereof, adjacent the peripheral notch. The flange is preferably hexagonal or otherwise shaped for cooperative engagement by a wrench or the like, for gripping the lower portion for removing it from a threaded bore.

16 Claims, 3 Drawing Sheets

U.S. PATENT DOCUMENTS

| | | |
|---|---|---|
| 3,812,757 | 5/1974 | Reiland . |
| 3,963,322 | 6/1976 | Cryctko . |
| 4,269,246 | 5/1981 | Larson et al. . |
| 4,492,500 | 1/1985 | Ewing . |
| 4,506,917 | 3/1985 | Hansen Arne . |
| 4,641,636 | 2/1987 | Cotrel . |
| 4,763,644 | 8/1988 | Webb . |
| 4,764,068 | 8/1988 | Crispell . |
| 4,790,297 | 12/1988 | Luque . |
| 4,815,453 | 3/1989 | Cotrel . |
| 4,838,264 | 6/1989 | Bremer et al. . |
| 5,005,562 | 4/1991 | Cotrel . |
| 5,067,955 | 11/1991 | Cotrel . |
| 5,073,074 | 12/1991 | Corrigan et al. . |
| 5,129,388 | 7/1992 | Vignaud et al. . |
| 5,147,360 | 9/1992 | Dubousset . |
| 5,154,719 | 10/1992 | Cotrel . |
| 5,261,907 | 11/1993 | Vignaud et al. . |
| 5,261,912 | 11/1993 | Frigg . |
| 5,282,707 | 2/1994 | Palm . |
| 5,312,404 | 5/1994 | Asher et al. . |
| 5,346,493 | 9/1994 | Stahurski et al. . |
| 5,364,400 | 11/1994 | Rego, Jr. et al. . |
| 5,382,248 | 1/1995 | Jacobson et al. . |
| 5,385,583 | 1/1995 | Cotrel . |
| 5,487,742 | 1/1996 | Cotrel . |
| 5,496,321 | 3/1996 | Puno et al. . |
| 5,499,892 | 3/1996 | Reed . |
| 5,507,747 | 4/1996 | Yuan et al. . |
| 5,562,663 | 10/1996 | Wisnewski et al. . |
| 5,630,817 | 5/1997 | Rokegem et al. . |
| 5,643,260 | 7/1997 | Doherty . |
| 5,653,710 | 8/1997 | Härle . |
| 5,697,929 | 12/1997 | Mellinger . |

SET SCREW FOR USE WITH OSTEOSYNTHESIS APPARATUS

CROSS REFERENCE TO RELATED APPLICATIONS

This application is a continuation in part of application Ser. No. 08/778,765, entitled SET SCREW FOR USE WITH OSTEOSYNTHESIS APPARATUS, filed Jan. 6, 1997.

BACKGROUND OF THE INVENTION

The present invention relates to improvements in set screws for use with apparatus for correcting orthopedic deformities and, in particular, for use in spinal osteosynthesis.

Surgically implanted spinal osteosynthesis apparatus often includes rods which are secured along at least a portion of the spine by a system of hooks, bone screws including sacral screws and pedicle screws and transverse connectors for the purpose of stabilizing and adjusting spinal alignment. In a very basic apparatus of this type, the hooks and bone screws include a spinal rod bore extending through a ring or body or head of the hook or screw. The screws are screwed into the pedicle portion of the vertebra at desired locations and a spinal rod is then extended through the spinal rod bore in each bone screw.

Where the bone screw has a rod receiving ring and the rod is to be fixed in position in the ring, a set screw is inserted in a threaded bore extending through a wall of the ring, so as to engage the rod, and is then tightened to fix the translational and rotational relationship of the rod within the ring. The rods may then be bent or shaped to maintain an adjacent portion of the spine in a desired configuration, to provide support to the spine and to exert desired corrective or stabilizing forces on the spine.

A slightly more complicated system uses transverse connectors in association with the bone screws to secure the spinal rods. The transverse connectors include an arm and a head. The head has a spinal rod bore extending therethrough. The arm of the connector is inserted through the spinal rod bore in the pedicle screw then the spinal rod may be inserted through the spinal rod bore in the transverse connectors. A threaded bore extends through the head of the connector perpendicular to the axis of the spinal rod bore. Once the rod is inserted through the bore in the transverse connectors the set screws are inserted through the threaded bores and tightened to fix the relative position of the rod within the spinal rod bore, and set screws are inserted in the threaded bores and tightened to fix the position of the transverse connector with respect to the pedicle screws.

The pedicle screws and transverse connectors may be of the closed type as discussed above or of an open end type wherein the head of the screw or connector generally incorporates a U-shaped groove. Several types of open end type bone screws have been previously used. One type of such screw is shown in the U.S. Patent of Cotrel U.S. Pat. No. 5,005,562. The device in the Cotrel patent has threaded interior surfaces on the two upright branches that form the rod receiving channel therebetween and which receive a threaded set screw having a rod engaging point and outer ring. The set screw in Cotrel is tightened against the rod by advancing the set screw along the threads. However, this system has limitations. In particular, the ability of the set screw of Cotrel to grip and hold the rod is heavily dependent on the torque applied to the set screw during installation. Unfortunately, the torque is limited because too much torque will cause the branches to spread, thereby allowing the set screw to loosen and the implant to fail. Such failure can also occur when forces are applied to the implant during use, such as at time of muscular stress or during accidents when the back is jolted. To try to overcome this problem associated with the Cotrel device, the implant branches and set screw are increased in size to add strength and/or a retention ring is placed around the outside of the branches to reduce the likelihood of expansion. However, the strengthening adds substantial bulk to an implant and a ring adds bulk and complexity to the implant. In implants, it is important to try to reduce bulk rather than add to it, as it is desirable for the implants to be as low profile as possible.

Rather than have a pair of branches joined only by a set screw or by a set screw and an exterior ring, a cap has been proposed which mates with the branches on opposite sides of the cap to prevent the branches from expanding radially outward upon application of torque to the set screw. The cap also closes off the open end of the bone screw after the rod is placed in the groove in the bone screw. The set screw is then inserted in a threaded bore in the cap and tightened to fix the position of the transverse connector with respect to a respective bone screw. A substantial torque can then be applied to the set screw while held in the surrounding threads of the cap without expanding the bone screw branches.

Various implants such as hooks, pedicle screws and transverse connectors used in the present invention may be of the closed type, as discussed above, or of an open end type, such as described above, wherein the head of the hook screw or connector generally incorporates a U-shaped groove or slot, an upper end of which may be closed off by a cap after a rod is placed in the open end so as to complete the rod bore. A threaded screw bore for the set screw typically extends through the cap.

The efficacy of the set screw is critical to the overall performance and efficiency of the osteosynthesis apparatus. The set screw must firmly secure the spinal rod or the arm of transverse connectors to prevent rotational or translational movement of the rod or arm after installation. Due to the nature of use of the set screw, it is important that the set screw be relatively small yet constructed to receive sufficiently high torque to firmly set the set screw and hold the rod. The set screw must also be easily manipulated to permit relatively rapid insertion and tightening during surgical procedures. It is also preferable that after insertion, no portion of the set screw extends beyond the threaded bore into which the set screw is inserted. The remaining portion of the set screw should be removable to facilitate disassembling of the osteosynthesis apparatus at any time. It is desirable that the set screw take advantage of physical penetration into the rod so as to improve the strength of the connection to resist axial movement of the rod relative to the set screw over that provided only by abutting friction.

Set screws have been previously developed with break-off heads or stems which break off after the set screw is inserted through a threaded bore and tightened to a preselected torque. Preferably, no portion of the set screw that remains after the head or stem breaks off extends above or beyond an outer edge of the threaded bore. However, prior art set screws normally have undesirable burrs that are left after the head breaks off that must be removed, thereby making the procedure more difficult or alternatively such burrs may lead to irritation of the patient, if not removed. Often, after installation, a set screw must be removed to reposition a rod or fix a broken apparatus. Prior art set screws have been difficult to remove after the head or stem is broken off. Consequently, it is desirable to have a set screw that can be comparatively easily removed even without a head.

It is also desirable to have a set screw that has an axially aligned tip that penetrates relatively deeply into a rod for preventing movement along or around the rod of an associated implant once tightened, but also includes structure that helps prevent rocking or translational movement of the set screw relative to the point of penetration. Rocking or movement of the screw relative to the location of penetration weakens the grip provided by the tip in the rod and the prevention of such movement substantially strengthens the juncture of the screw and the rod. The set screw tip, such as a point can only penetrate deeply into the rod if sufficient torque can be applied to the set screw to do so. In general greater torque is available due to greater bulk or due to special construction that allows greater strength without adding bulk. The latter is preferred in implants.

It is also desirable to have a set screw that is relatively easy to manufacture to help keep the cost of the screws down.

In general, there is still a need for an improved set screw which is quite strong in size, reliable in securing an osteosynthesis apparatus in place without burrs or high profile, is easily removable and is relatively small yet easily manipulable to facilitate its insertion and removal.

SUMMARY OF THE INVENTION

The present invention comprises an improved set screw for use in an osteosynthesis apparatus primarily for securing and fixing the relative position of a rod within a rod receiving bore of another implant. The set screw has a head or stem preferably having a hexagonal external cross-section, and a lower portion having a threaded outer surface. A peripheral break notch preferably is formed between the head and the lower threaded portion of the set screw to facilitate breaking and separation of the two portions upon threading of the lower portion into a threaded bore of a spinal implant. The lower threaded portion includes a feature which facilitates subsequent removal of the lower threaded portion from the threaded bore in which it is secured.

In a first embodiment, the feature facilitating removal, comprises a bore which extends completely through the screw, from top to bottom. The bore may be cylindrical and adapted to receive an easy out tool for removal of the lower threaded portion, or of a geometry which corresponds to the shape of an allen type wrench which may be inserted in the section of the bore extending into the lower threaded portion of the screw for use in removal of the lower threaded portion.

In another embodiment, a flange is formed on the lower threaded portion of the screw at an upper end thereof, adjacent the peripheral notch. The flange is preferably hexagonal, but includes at least one flat edge. Once the screw is installed and the head sheared off, a wrench, sized and shaped to cooperatively engage the flange, may be used to remove the lower threaded portion.

In the second embodiment, a tip is centrally formed on a lower surface of the set screw so as to be coaxially aligned with the axis of the set screw. Both embodiments also include a ring having a sharp lower edge that encircles the lower surface of the set screw at the outer periphery thereof. The point and ring are adapted to penetrate into a rod secured within a rod receiving implant to further stabilize the resulting structure.

OBJECTS AND ADVANTAGES OF THE INVENTION

The objects and advantages of the invention include: providing a set screw for use in an osteosynthesis apparatus for securing a rod or elongate member from rotational and translational movement within a bore of a securement ring or body; providing such a set screw which is relatively small, yet which can be readily manipulated; providing such a set screw which includes a head or stem which breaks off during tightening at a preselected torque after the set screw has been tightened down; to provide such a set screw which includes a peripheral break inducing and directing notch on an outer surface of the screw between the head or stem of the screw and a lower threaded portion thereof; to provide such a set screw which includes a tip, point or pointed edge for biting or penetrating into the rod to be secured by the set screw; to provide such a set screw incorporating means for facilitating removal of the head of the set screw after it has been broken off; to provide such a set screw which incorporates means for facilitating removal of the lower threaded portion of the set screw when desired; and to provide such a set screw which is relatively simple to manufacture and particularly well suited for its intended uses thereof.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 7:
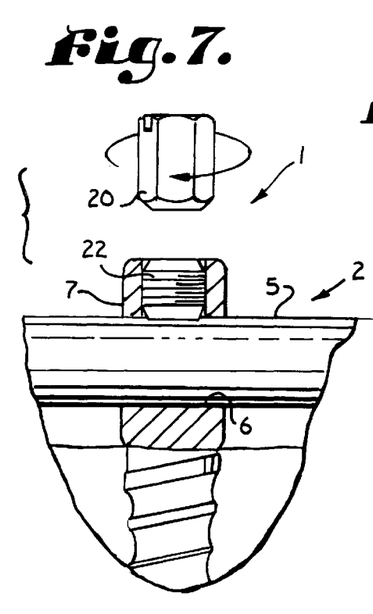
FIG. 7 is a front elevational view on a reduced scale of the set screw showing a lower threaded portion of the set screw engaging a spinal rod secured within a spinal rod bore in a bone screw and showing a head or stem of the set screw after being broken off.
Figures 8, 11:
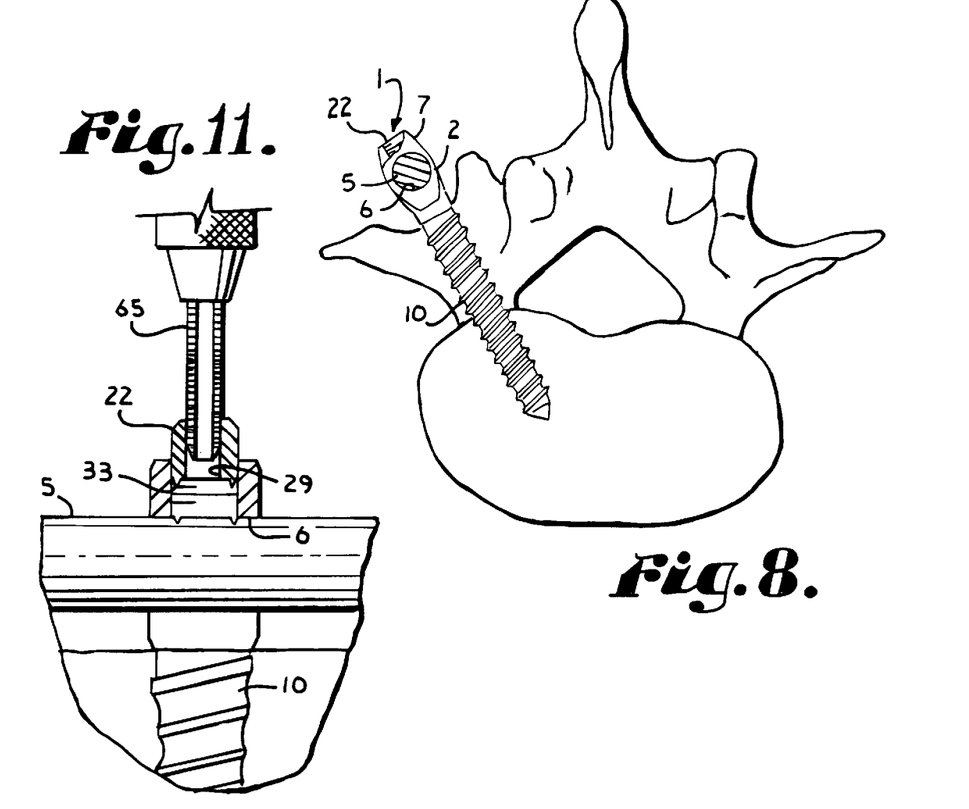
FIG. 8 is a side elevational view on a reduced scale of a bone screw secured within a vertebra and with portions broken away to show a lower threaded portion of the set screw of the present invention secured within the bone screw.
FIG. 11 is a front elevational view similar to FIG. 6 showing use of an easy out type tool to remove a lower threaded portion of the set screw of the present invention from a bone screw.

Referring to the drawings in more detail, and in particular FIGS. 1 through 4, the reference numeral 1 generally refers to a set screw for use in osteosynthesis apparatus and in particular for use in spinal osteosynthesis apparatus 2 as shown in FIGS. 7 and 8. Referring to FIGS. 7 and 8, the set screw 1 is adapted for use in securing a rod 5 of the apparatus 2 relative to a rod receiving bore 6 of a head or ring 7, from translational or rotational motion. The ring 7 is of the type formed in the head of a bone screw 10 or the head of a connector or bone hook (not shown) secured to the bone screw 10. In the field of spinal osteosynthesis, the bone screws 10 are often referred to as sacral screws or pedicle screws. The rod 5 may be of the type including spinal rods or the arm or rod portion of a connector. The illustrated rod 5 is round; however, it is foreseen that the rod could be square to help prevent rotation in a similarly shaped bore in the bone screw 10, or have a cross section of almost any shape. A threaded set screw receiving bore 11 extends through the ring 7 perpendicular to the axis of the rod receiving bore 6 and extends radially relative to the ring 7 for the closed hooks, screws and connectors. For open hooks, screws and connectors the angle of point of penetration on the rod may vary with respect to the axis of the rod and to the design for a closing cap thereof.

The set screw 1, as shown in FIGS. 1 through 4, comprises a head or stem 20, of hexagonal external crosssection and a lower portion 22, having a threaded outer circumferential surface 23. The head 20 is relatively elongated to facilitate manipulation of the set screw 1. A peripheral break or shear inducing notch 25 is formed between the head 20 and the lower threaded portion 22 of the set screw 1 on an outer surface 26 of the set screw 1. The notch 25 is positioned and sized to initiate breakage along the radially innermost portion thereof at the level of the notch 25 and at a preselected torque without forming substantial burrs on the resulting upper surface of the set screw lower portion 22.

Figure 1:
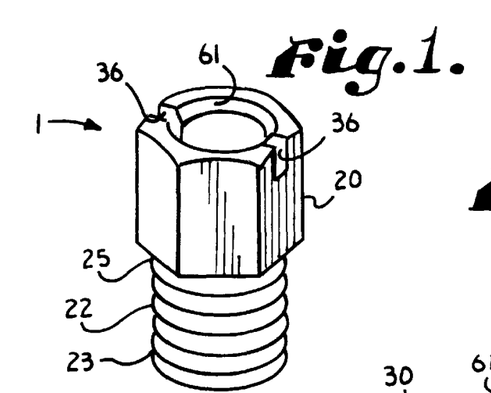
FIG. 1 is a perspective view of a set screw in accordance with the present invention.
Figure 2:
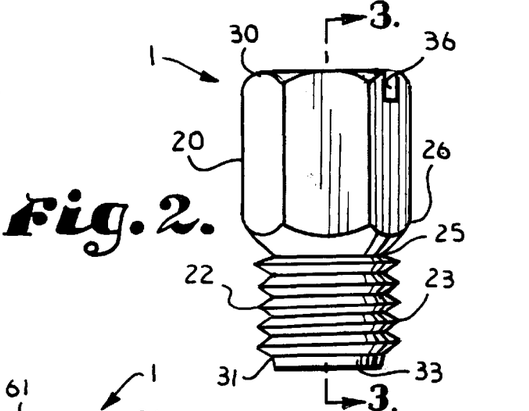
FIG. 2 is a front elevational view of the set screw of the present invention.
Figure 3:
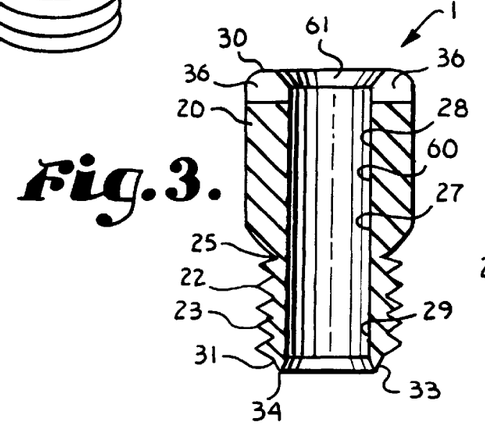
FIG. 3 is a cross-sectional view of the set screw, taken along line 3—3 of FIG. 2 showing a cylindrical bore extending therethrough.
Figure 4:
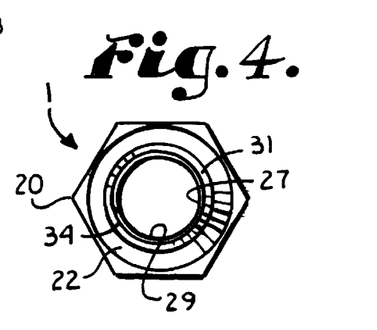
FIG. 4 is a bottom plan view of the set screw of the present invention.
Figure 5:
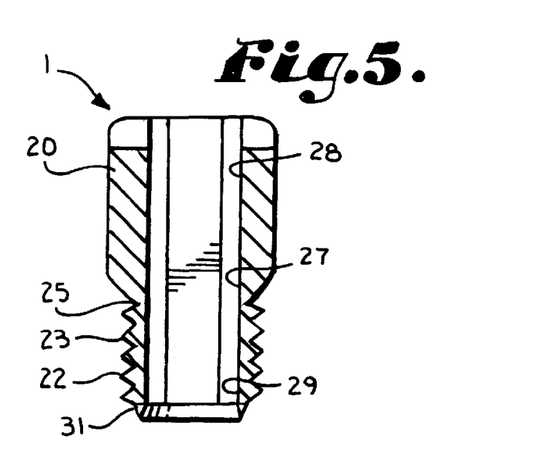
FIG. 5 is a cross-sectional view, similar to FIG. 3 showing a similar set screw with a hexagonal bore extending therethrough.
Figure 6:
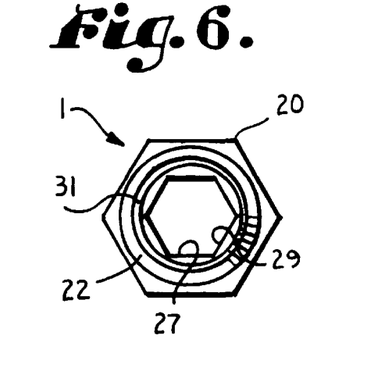
FIG. 6 is a bottom plan view of the embodiment shown in FIG. 5.

As best seen in FIG. 3, a cylindrical bore or projection receiving bore 27, comprising an upper bore section 28 and a lower bore section 29 is formed in the set screw 1 and extends completely through the set screw 1 from an upper end 30 of the head 20 through a lower end 31 of the lower portion 22. Although in a preferred embodiment the bore 27 is cylindrical, it is foreseen that the bore 27 may be of a wide variety of shapes including hexagonal as shown in FIGS. 5 and 6 in which the same reference numerals are used to identify equivalent elements. The upper bore section 28 extends coaxially through the head 20 of the screw 1 and the lower bore section 29 extends coaxially through the lower threaded portion 22 of the screw 1. The lower bore section 29 may be of slightly smaller diameter than the upper bore section 28.

A ring 33 is formed on and extends downward from the lower end 31 of the set screw 1. The ring extends 360 degrees around the outer periphery of the lower end 31. A lower edge 34 of the ring 33 is sharpened and adapted to cut into a rod 5 when urged thereagainst.

A drive slot 36 is located at the upper end 30 of the set screw head 20. The slot 36 is a rectangular notch extending downward from the upper end 30 with portions on diagonally opposite sides of the screw 1. The set screw 1 is preferably driven by a hexagonal socket type wrench 39, partially shown in FIGS. 8 and 9 The slot 36 can receive mating parts of the wrench 39; however, the drive slot 36 is adapted to also receive a flat head screwdriver type tool for starting the set screw 1 into the threaded set screw bore 11 in some applications.

In use, the set screw 1 may be inserted in the set screw receiving bore 11 in the ring 7 after the bone screw 10 is inserted into a bone 40 of a patient and after a rod 5 is inserted through the rod receiving bore 6. To secure the rod 5 in position, thereby preventing further rotational or translational movement of the rod 5 with respect to the rod receiving bore 6, the set screw 1 is further driven through the set screw receiving bore 11 until the lower edge 34 of the ring 33 engages and bites into the rod 5. Further driving or tightening of the set screw 1 produces a preselected torque on the head 20 and causes the head 20 of the set screw 1 to shear off along the radially innermost portion of the peripheral notch 25, as shown in FIG. 6. The bone 11 and the penetration of the ring 33 into the rod 5 stabilizes the set screw 1 relative to the rod 5, so that the set screw 1 is able to secure the rod 5 and prevent relative movement of the rod 5 with respect to the bone screw 10 even under substantial load.

The lower threaded portion 22 of the set screw 1 is preferably sized such that after the head 20 is sheared off, an upper surface 45 of the set screw lower portion 22 is generally flush with an upper edge or upper surface 47 of the ring 7 such that no portion of the set screw lower portion 22 extends beyond the upper surface 47 of the ring 7. Further, after the head 20 is sheared off, the upper surface 45 of the set screw lower portion 22 is generally free from burrs or jagged edges.

The set screw 1 may also be pre-loaded into the bone screw 10, or related structure, prior to insertion into the patient. In particular, the set screw 1 may be manually inserted in the threaded set screw receiving bore 11 of a bone screw 20 or a connector before insertion in a patient and rotated a sufficient number of turns such that the set screw 1 is secured in the set screw receiving bore 11, but such that the sharpened ring 34 does not extend substantially into the rod receiving bore 6. The bone screw 10, with the set screw 1 secured thereto, may then be secured into the appropriate bone 40 of a patient. After a rod 5 is inserted through the rod receiving bore 6 of the bone screw 10, the set screw 1 is tightened, as discussed above.

Figure 9:
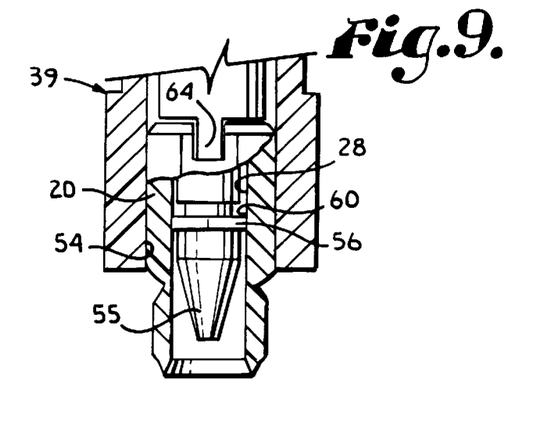
FIG. 9 is a fragmentary front elevational view of the set screw shown secured within a socket wrench with portions broken away to show detail.
Figure 10:
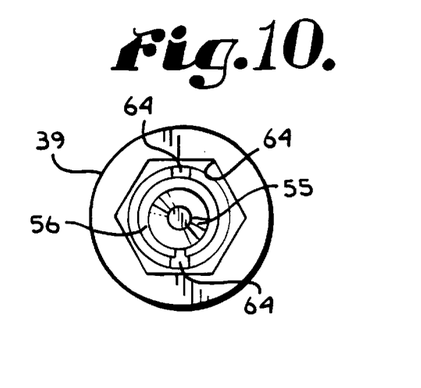
FIG. 10 is a bottom plan view of the socket wrench, as shown in FIG. 9, without a set screw secured therein.

The upper bore section 28 of the set screw 1 is adapted to facilitate removal of the set screw head 20 once it is sheared off from the lower threaded portion 22. The set screw is adapted for use with the socket type torque wrench 39, as shown in FIGS. 9 and 10, having a hexagonal socket 54 and a male member or projection 55 extending centrally in the socket. The projection 55 includes a resilient biasing member 56 circumferentially secured thereon. The projection 55 is sized for insertion into at least the upper bore section 28 when the set screw head 20 is positioned in the socket 54. The resilient biasing member 56 biases against an internal wall 60 of the head 20 defining the upper bore section 28 to grip the head 20.

The internal wall 60 has a chamfer 61 at the upper end 30 of the set screw head 20 to facilitate insertion of the projection 55 into the bore 27 in part by facilitating compression of the resilient biasing member 56. The resilient biasing member 56, as shown in FIGS. 9 and 10, generally comprises a split washer type spring, however it is foreseen that the biasing element 56 may be of a wide range of configurations and structures. Further other retention means for releasably securing the set screw 1 to the projection 55 may be utilized including a rubber washer, magnetic coupling means, and various structure producing an interference fit between the projection 55 and the bore 27. Further it is foreseen that means may be provided for gripping of the head 20 by the wrench 39 or related torque inducing tool by engagement of the exterior surface of the head 20.

The projection 55 may include a pair of drive projections or tabs 64 extending laterally from opposite sides of the projection 55 and adapted to mate with the drive slot 36 extending across the upper end 30 of the set screw head 20 to permit an installing surgeon to drive or rotate the set screw 1 by the projection 55.

After the head 20 has been sheared off from the set screw lower threaded portion 22, the lower bore section 29 is adapted to receive an easy out type tool 65 to permit removal of the set screw lower portion 22 when necessary and as is shown in FIG. 11.

The bone screws 10 and related connectors (not shown) discussed above are of a closed end variety in that the ring 7 is of one piece construction. The set screws 1 of the present invention are also adapted for use with bone screws and connectors of the open end variety (not shown). In the open end variety, the ring 7 includes a generally U-shaped groove opening along an upper end of the head or ring 7. A saddle or cap is securable to the head 7 to close off the groove and form the rod receiving bore 6. The set screw receiving bore 11 may be formed in the cap or another part of the head 7.

Referring to FIGS. 12 through 15, the reference numeral 70 refers to a second embodiment of the present invention. The set screw 70 includes a first head 71 and a lower portion 72. The lower portion 72 includes a second head 74 at an upper end thereof and a threaded outer surface 75 on a lower section 76 thereof. Outer surfaces of both the first and second heads 71 and 74 are hexagonal for engagement by a wrench. The second head 74 generally comprises a hexagonal shaped flange extending outward from the threaded lower section 76. It is foreseen that the shape of the first and second heads 71 and 74 may be of various configurations or shapes which provide a surface adapted for cooperative engagement by a torque inducing tool such as a wrench.

Figure 12:
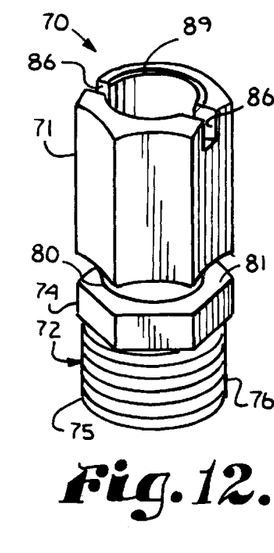
FIG. 12 is a perspective view of an alternative embodiment of a set screw in accordance with the present invention.
Figure 13:
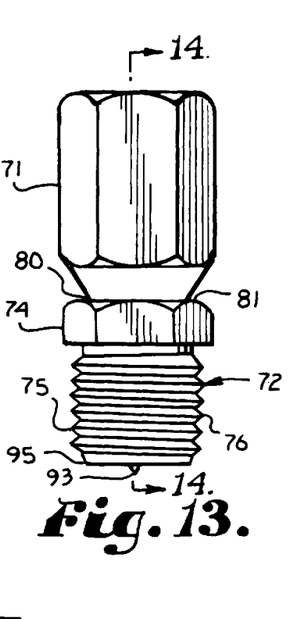
FIG. 13 is a front elevational view of the embodiment shown in FIG. 12.

A peripheral break or shear inducing notch 80 is formed on an outer surface of the set screw 70, between the first head 71 and the second head 74, adjacent an upper end 81 of the second head 74. The notch 80 is positioned and sized to initiate breakage along the radially innermost portion thereof at the level of the notch 80 and at a preselected torque without forming substantial burrs on the resulting upper surface of the set screw lower portion 72.

Figure 14:
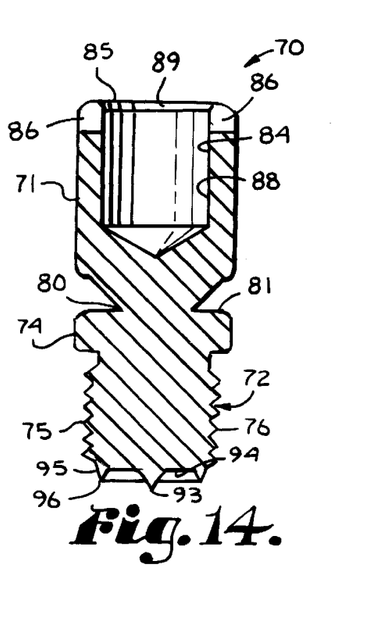
FIG. 14 is a cross-sectional view of the alternative embodiment of the set screw, taken along line 14—14 of FIG. 13.

As best seen in FIG. 14, a cylindrical bore or projection receiving bore 84 is formed in the set screw 70 and extends into the first head 71 of the set screw 70 from an upper end 85 thereof. In the preferred embodiment, the bore 84 only extends into the first head 71 and not into the lower portion 72 of the set screw 70. However, it is foreseen that the bore 84 could extend partially into the lower portion 72 or completely therethrough as in the first embodiment discussed above.

A drive slot 86 is located at the upper end 85 of the set screw head 71. The slot 86 is a rectangular notch extending downward from the upper end 85 with portions on diagonally opposite sides of the screw 70. The set screw 70 is preferably driven by a hexagonal socket type wrench 39 as described above and partially shown in FIG. 9 in use with the set screw 1 of the first embodiment. The slot 86 can receive mating parts of the wrench 39; however, the drive slot 86 is adapted to also receive a flat head screwdriver type tool for starting the set screw 70 into the threaded set screw bore 11 in some applications.

The bore 84 of the set screw 70 is adapted to facilitate removal of the set screw head 71 once it is sheared off from the lower portion 72. The set screw 70 is adapted for use with the socket type torque wrench 39 as discussed above and as shown in FIGS. 9 and 10 in use with the set screw 1 of the first embodiment. The bore 84 is sized for receipt of the projection 55 when the set screw first head 71 is positioned in the socket 54. The resilient biasing member 56 biases against an internal wall 88 of the head 71 defining the bore 84 to grip the first head 71.

The internal wall 88 has a chamfer 89 at the upper end 85 of the set screw first head 71 to facilitate insertion of the projection 55 into the bore 84 in part by facilitating compression of the resilient biasing member 56.

The drive slot 86 of the set screw first head 71 is adapted to receive the drive tabs 64 on the projection 55 to permit an installing surgeon to drive or rotate the set screw 70 with the projection 55.

Figure 15:
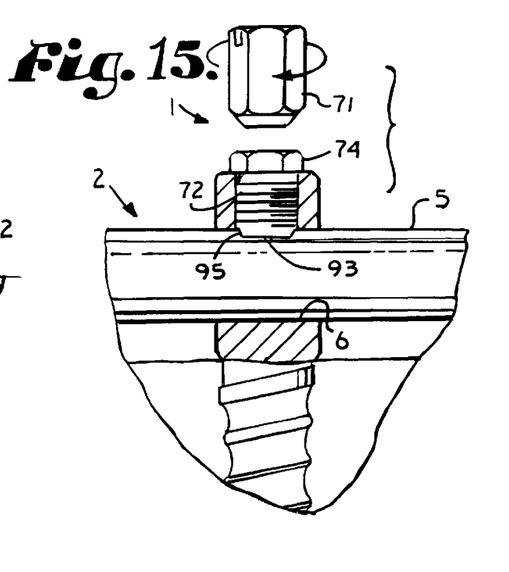
FIG. 15 is a front elevational view on a reduced scale of the alternative embodiment of the set screw, as in FIG. 12, showing a lower threaded portion of the set screw engaging a spinal rod secured within a spinal rod bore in a bone screw and showing a head or stem of the set screw after being broken off.

After the first head 71 has been sheared off from the set screw lower portion 72 as generally shown in FIG. 15, the second head 74 is shaped for engagement by a wrench to permit removal of the set screw lower portion 72 when necessary.

As best seen in FIG. 14, a tip, illustrated as a point 93, is formed on a lower surface 94 of the set screw 70 centrally thereof so as to extend outward along a central axis of rotation of the set screw 70. The point 93 forms a point receiving notch, depression, or indentation in the rod against which it is driven. A ring 95 is formed on and extends downward from the lower surface 94 of the set screw 70. The ring 95 extends 360 degrees around the outer periphery of the lower end 94. A lower edge 96 of the ring 95 is sharpened and adapted to cut into a rod 5 when urged thereagainst. The point 93 preferably extends axially outward and downward further than the ring 95 so as to penetrate deeper into the rod 5 during use.

It is noted that while the set screws of the present invention may be used in conjunction with knurled rod, knurlling causes the rod to be weakened and fail more easily. Therefore, it is normally preferable to use the set screws of the invention with smooth surface rod. The set screws of the present invention are especially effective in penetrating into and preventing relative motion between the set screw and smooth rod. In addition the set screws of the present invention can be applied with a relatively high torque because the bore in which the set screw is received is closed and completely surrounds the set screw so that it does not spread during torquing and such that the set screws of the present invention can relatively deeply penetrate into rod, especially smooth rod, and hold securely against relative movement while stabilizing the screw with respect to the rod, even when the screw is positioned in the closure cap of an open ended implant. The set screws of the present invention may also be relatively small, for example 5.5 mm. in diameter, and still provide a strong and stable positional stabilization of an associated implant relative to a rod received in the implant.

It is also foreseen that in some specialized uses of the set screw that the set screw will be configured to incorporate a stabilizing structure, but that the head will not be removable, that is, broken from the remainder of the set screw upon application of torque. In such instances the head will normally be solid without an interior bore, but such a head could also include an interior bore for receiving a tool for guidance or control during installation.

It is to be understood that while certain forms of the present invention have been illustrated and described herein, it is not to be limited to the specific forms or arrangement of parts described and shown.

What is claimed and desired to be secured by letters patent is as follows:

1. A set screw for use in a osteosynthesis apparatus; said set screw being sized and shaped to be received in a first element of the apparatus and to be urged against a second element of the apparatus in order to secure the first and second elements together; said set screw comprising:
   a) a head shaped for engagement by a torque inducing tool;
   b) a lower portion having a threaded outer surface threaded, sized and shaped to be threadedly received in a threaded bore of the first element;
   c) a peripheral notch formed in an outer surface of said set screw between said head and said lower threaded portion for inducing shear of said head from said lower portion upon application of sufficient torque on said head relative to said lower portion;
   d) a bore extending completely through said head and said lower portion of said set screw from an upper surface of said set screw to a lower surface thereof; and
   e) a penetrating tip on said set screw lower surface for operatively penetrating into the first element.

2. The set screw as disclosed in claim 1 wherein:
   a) a drive notch is formed in and across an upper end of said head.

3. The set screw as disclosed in claim 2 wherein:
   a) said head is elongated relative to said lower threaded portion for facilitating manipulation and torquing thereof.

4. The set screw as disclosed in claim 1 including:
   a) a ring formed on said lower surface thereof and having a sharpened lower edge.

5. The set screw as in claim 1 wherein:
   a) said bore is cylindrical.

6. The set screw as in claim 1 wherein:
   a) a portion of an inner wall of said set screw defining said bore is planar.

7. The set screw as in claim 1 wherein:
   a) a portion of said bore extending through said head is hexagonal.

8. In combination with the set screw as disclosed in claim 1 an implant having a threaded bore for receiving said set screw wherein said threaded bore entirely encircles a threaded portion of said set screw.

9. A set screw for use in a osteosynthesis apparatus comprising:
   a) a first head shaped for engagement by a torque inducing tool;
   b) a lower portion having a threaded outer surface on a lower section thereof and having a second head formed at an upper end thereof; said second head shaped for engagement by a torque inducing tool; and
   c) a peripheral notch formed in an outer surface of said set screw between said first head and said second head for inducing shear of said first head from said lower portion upon application of sufficient torque on said first head relative to said lower portion;
   d) a bore extending into said first head from an upper end thereof;
   e) a point formed centrally on a lower surface of said set screw lower portion and extending outward therefrom; said point extends coaxially with a longitudinal axis of said set screw; said point adapted to penetrate into a surface of an elongate member against which the set screw is operably advanced; said set screw longitudinal axis operably being adapted to intersect with a central axis of said elongate member; and
   f) a ring spaced from and in surrounding relationship to said point; said ring having a sharpened outer edge.

10. The set screw as disclosed in claim 9 wherein:
    a) said point extends axially outward from a remainder of said set screw substantially further than said ring.

11. The set screw as disclosed in claim 9 wherein:
    a) a drive notch is formed in and across an upper end of said first head.

12. The set screw as disclosed in claim 9 wherein:
    a) said first head is elongated relative to said lower portion for facilitating manipulation and torquing thereof.

13. In combination with the set screw as disclosed in claim 9 an implant having a threaded bore for receiving said set screw wherein said threaded bore entirely encircles a threaded portion of said set screw.

14. In combination, a set screw with a medical implant having a first elongate member and a second member; said set screw operably securing said first member having a central axis to said second member; said combination wherein:
    a) said second member includes a threaded bore operably fully encircling and threadably receiving said set screw and operably providing for advancement of said set screw toward and against said first member under torque;
    b) said set screw including a head adapted to receive a tool for rotating and advancing the screw in said threaded bore;
    c) said set screw having a threaded portion attached to said head such that during installation of said set screw into said threaded bore, said set screw advances toward and then against said first member; said threaded portion having a lower surface;
    d) said head is breakably attached to said threaded portion; said head being attached to said threaded portion in a manner such that when a predetermined torque is applied to said head during installation of said set screw, said head separates from said threaded section;

e) said set screw having a central elongate axis of rotation adapted to intersect with the first member central axis during usage;

f) said set screw having a bore extending completely therethrough along said central elongate axis or rotation; and g) said threaded portion lower surface having a penetrating point extending therefrom and surrounding said pass through bore; said point operatively penetrating said first elongate member as said set screw advances in said second member.

15. The combination according to claim 14 wherein:

a) said elongate member is a rod having a smooth outer surface; and b) said second member includes a threaded bore for receiving and completely encircling said set screw and maintaining the axis of said set screw perpendicular to the axis of said first member.

16. The combination according to claim 15 including:

a) a ring depending from said set screw around an outer periphery of a lower surface of said set screw; said ring having a sharp lower edge and being positioned such that said ring partially penetrates the elongate member during use.

* * * * *